US011897318B2

(12) United States Patent
Line et al.

(10) Patent No.: US 11,897,318 B2
(45) Date of Patent: Feb. 13, 2024

(54) AIR SANITIZING APPARATUS FOR INTERIOR OF VEHICLE AND METHOD OF SANITIZING AIR IN THE VEHICLE USING THE APPARATUS

(71) Applicant: Ford Global Technologies, LLC, Dearborn, MI (US)

(72) Inventors: Johnathan Andrew Line, Northville, MI (US); Michael Kolich, Windsor (CA); Daniel Ferretti, Commerce Township, MI (US); Scott H. Dunham, Redford, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 370 days.

(21) Appl. No.: 17/325,615

(22) Filed: May 20, 2021

(65) Prior Publication Data

US 2021/0268878 A1 Sep. 2, 2021

Related U.S. Application Data

(62) Division of application No. 16/227,662, filed on Dec. 20, 2018, now Pat. No. 11,040,601.

(51) Int. Cl.
*B60H 3/00* (2006.01)
*B60H 1/00* (2006.01)
(Continued)

(52) U.S. Cl.
CPC ....... *B60H 3/0078* (2013.01); *B60H 1/00371* (2013.01); *A61L 9/22* (2013.01);
(Continued)

(58) Field of Classification Search
CPC .. B60H 3/0078; B60H 3/0021; B60H 3/0035; B60H 3/0633; B60H 1/00471;
(Continued)

(56) References Cited

U.S. PATENT DOCUMENTS 3,884,048 A 5/1975 Schneider
5,507,234 A * 4/1996 Thorsen .................... B66C 9/16
212/275

(Continued)

FOREIGN PATENT DOCUMENTS

DE 102018002328 A1 9/2019
EP 2668964 A1 12/2013
(Continued)

*Primary Examiner* — Allen R. B. Schult
(74) *Attorney, Agent, or Firm* — Vichit Chea; Price Heneveld LLP

(57) ABSTRACT

An air sanitizing apparatus for a vehicle comprising: an ozone generator; a negative ion generator; and an ultraviolet radiation source. The air sanitizing apparatus further includes a rotating feature and a motor operably connected to the rotating feature, the rotating feature configured to move the air sanitizing apparatus along a track system. The air sanitizing apparatus can includes a first end portion; a second end portion; a middle portion disposed between the first end portion and the second end portion, the middle portion rotatable relative to the first end portion and the second end portion about an axis that extends through both the first end portion and the second end portion. The ozone generator, the negative ion generator, and the ultraviolet radiation source are all disposed at the middle portion. The air sanitizing apparatus is disposed in an interior of a vehicle below but adjacent to a ceiling.

16 Claims, 13 Drawing Sheets

(51) Int. Cl.
  *A61L 9/22*   (2006.01)
  *B01D 46/00*  (2022.01)
  *B03C 3/68*   (2006.01)
  *B01D 46/66*  (2022.01)
  *B60H 3/06*   (2006.01)

(52) U.S. Cl.
  CPC ...... *A61L 2209/111* (2013.01); *A61L 2209/14* (2013.01); *A61L 2209/16* (2013.01); *B01D 46/0028* (2013.01); *B01D 46/785* (2022.01); *B03C 3/68* (2013.01); *B60H 3/0021* (2013.01); *B60H 3/0035* (2013.01); *B60H 3/0633* (2013.01)

(58) Field of Classification Search
  CPC ........ B03C 3/68; A61L 9/22; A61L 2209/111; A61L 2209/14; A61L 2209/16; A61L 2202/14; A61L 2202/25; B01D 46/0029; B01D 46/0078
  USPC .......................................................... 454/156
  See application file for complete search history.

(56) References Cited

U.S. PATENT DOCUMENTS

| | | | |
|---|---|---|---|
| 6,908,597 B2 | 6/2005 | Chen et al. | |
| 9,149,549 B2 | 10/2015 | Kreitenberg | |
| 9,592,312 B2 | 3/2017 | Yslo et al. | |
| 10,376,605 B1 | 8/2019 | Majdali et al. | |
| 2002/0098109 A1 | 7/2002 | Nelson et al. | |
| 2004/0129770 A1* | 7/2004 | Masuno | G06Q 30/00 235/375 |
| 2005/0186108 A1* | 8/2005 | Fields | A61L 2/202 422/123 |
| 2007/0053188 A1 | 3/2007 | New et al. | |
| 2007/0207066 A1 | 9/2007 | Thur et al. | |
| 2008/0175761 A1 | 7/2008 | Thur et al. | |
| 2010/0237649 A1 | 9/2010 | Concina | |
| 2016/0000951 A1 | 1/2016 | Kreiner et al. | |
| 2016/0089459 A1 | 3/2016 | Boodaghians et al. | |
| 2016/0250362 A1 | 9/2016 | Mackin | |
| 2017/0217284 A1* | 8/2017 | Ji | B60H 1/00821 |
| 2017/0225541 A1 | 8/2017 | Shimoda et al. | |
| 2017/0297537 A1* | 10/2017 | Yako | A61L 2/22 |
| 2018/0065126 A1 | 3/2018 | Abate et al. | |
| 2018/0105394 A1 | 4/2018 | Hill et al. | |

FOREIGN PATENT DOCUMENTS

| | | |
|---|---|---|
| JP | 2011073617 A | 4/2011 |
| KR | 0124687 Y1 | 8/1998 |
| KR | 100602727 B1 | 7/2006 |

\* cited by examiner

AIR SANITIZING APPARATUS FOR INTERIOR OF VEHICLE AND METHOD OF SANITIZING AIR IN THE VEHICLE USING THE APPARATUS

CROSS-REFERENCE TO RELATED APPLICATION

This patent application is a division of U.S. patent application Ser. No. 16/227,662, which was filed on Dec. 20, 2018, entitled "AIR SANITIZING APPARATUS FOR INTERIOR OF VEHICLE AND METHOD OF SANITIZING AIR IN THE VEHICLE USING THE APPARATUS", which is incorporated herein in its entirety by reference.

FIELD OF THE INVENTION

The present invention generally relates to a vehicle mounted apparatus to sanitize the air and, in some embodiments, surfaces in the vehicle.

BACKGROUND OF THE INVENTION

Air in the interior of a vehicle can harbor microorganisms and chemicals that can adversely affect the health of a passenger breathing the air and cause malodorous odors. The thought of such microorganisms and chemicals can be especially discomforting to anticipated passengers of a vehicle-for-hire, commercial airplane, or passenger railcar. Such vehicles are more likely to have transported passengers who communicated airborne microorganisms or had malodorous animals in tow.

SUMMARY OF THE INVENTION

According to a first aspect of the present invention, an air sanitizing apparatus for a vehicle comprises: an ozone generator; a negative ion generator; and an ultraviolet radiation source.

Embodiments of the first aspect of the invention can include any one or a combination of the following features:
- a rotating feature and a motor operably connected to the rotating feature, the rotating feature configured to move the air sanitizing apparatus along a track system;
- a middle portion disposed between a first end portion and a second end portion, the middle portion rotatable relative to the first end portion and the second end portion about an axis that extends through both the first end portion and the second end portion;
- the ozone generator, the negative ion generator, and the ultraviolet radiation source are all disposed at the middle portion;
- the first end portion and the second end portion each including a rotating feature and a motor operably connected to the rotating feature, the rotating feature configured to move the air sanitizing apparatus along a track system;
- the middle portion including a rounded extension;
- one or more of the first end and the second end including rounded indents positioned to selectively receive the rounded extension of the middle portion depending on a degree of rotation of the middle portion;
- an air flow tube having an inside through which air can flow;
- an exhaust fan disposed at an end of the air flow tube and configured to cause air to flow through the inside of the air flow tube; and
- the ultraviolet radiation source is configured to irradiate ultraviolet radiation into the inside of the air flow tube.

According to a second aspect of the present invention, a vehicle comprises: a ceiling; an interior with air disposed therein; and an air sanitizing apparatus disposed in the interior below but adjacent to the ceiling, the air sanitizing apparatus including an ozone generator that, when activated, generates ozone into the interior, a negative ion generator that, when activated, negatively ionizes molecules in the air of the interior of the vehicle; and an ultraviolet radiation source that, when activated, irradiates the air of the interior with ultraviolet radiation.

Embodiments of the second aspect of the invention can include any one or a combination of the following features:
- a track system;
- the air sanitizing apparatus cooperating with the track system to move the air sanitizing apparatus selectively forward or rearward within the interior of the vehicle;
- the air sanitizing apparatus further including a rotating feature and a motor operably connected to the rotating feature, the rotating feature cooperating with the track system to move the air sanitizing apparatus along the track system;
- the track system including a first track and a second track;
- the air sanitizing apparatus further including a first end portion disposed adjacent the first track, a second end portion disposed adjacent the second track, and a middle portion disposed between the first end portion and the second end portion, the middle portion rotatable relative to the first end portion and the second end portion about an axis that extends through both the first end portion and the second end portion, and the axis is at least approximately orthogonal to the first track and the second track;
- one or more of the first end portion and the second end portion include a rotating feature and a motor operably connected to the rotating feature;
- a controller in communication with the ozone generator, the negative ion generator, the ultraviolet radiation source, and the motor connected to the rotating feature;
- the controller further in communication with locks of doors of the vehicle, motors that raise or lower windowpanes of the vehicle, and an occupancy sensor that senses whether an occupant is occupying the interior;
- the controller is configured to activate the ozone generator to generate ozone into the interior only when the locks of the doors are preventing access into the interior, the motors have fully raised the windowpanes, and the occupancy sensor indicates that no occupant is occupying the interior;
- a first row of seating;
- a second row of seating;
- the controller is configured to manipulate the motor to cause the air sanitizing apparatus to move along the track system past the first row of seating and above the second row of seating, and cause the negative ion generator to negatively ionize molecules in the air of the interior of the vehicle and the ultraviolet radiation source to irradiate the air of the interior with ultraviolet radiation while the air sanitizing apparatus is positioned above the second row of seating;
- the air sanitizing apparatus further includes: an air flow tube having an inside through which air can flow; and an exhaust fan disposed at an end of the air flow tube and configured to cause air to flow through the inside of the air flow tube;

the ultraviolet radiation source is configured to irradiate ultraviolet radiation into the inside of the air flow tube; and the vehicle is a bus used to provide intercity bus service.

According to a third aspect of the present invention, a method of sanitizing air in a vehicle comprises: upon request of an anticipated passenger of a seat in a vehicle, before the anticipated passenger occupies the seat, moving an air sanitizing apparatus from a first position that is not above the seat of the vehicle to a second position above the seat of the vehicle; and causing the air sanitizing apparatus to perform at least one of the following actions: generate ozone; negatively ionize molecules in interior air; and irradiate interior air with ultraviolet radiation.

Embodiments of the third aspect of the invention can include any one or a combination of the following features:
- moving the air sanitizing apparatus away from the second position, before the anticipated passenger occupies the seat;
- the anticipated passenger requested the air sanitizing apparatus to perform the at least one action via an application program on an electronic device located outside of an interior of the vehicle;
- the vehicle includes a track system, and the air sanitizing apparatus cooperates with the track system to move from the first position to the second position over the seat;
- the vehicle is a bus, a railway passenger car, or an airplane; and
- the air sanitizing apparatus is caused to perform both the actions of: negatively ionizing molecules in the interior air; and irradiating interior air with ultraviolet radiation.

These and other aspects, objects, and features of the present invention will be understood and appreciated by those skilled in the art upon studying the following specification, claims, and appended drawings.

DETAILED DESCRIPTION OF THE PREFERRED EMBODIMENTS

For purposes of description herein, the terms "forward," "rearward," and "below," and derivatives thereof, shall relate to the invention as oriented in FIG. 1. However, it is to be understood that the invention may assume various alternative orientations, except where expressly specified to the contrary. It is also to be understood that the specific devices and processes illustrated in the attached drawing, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
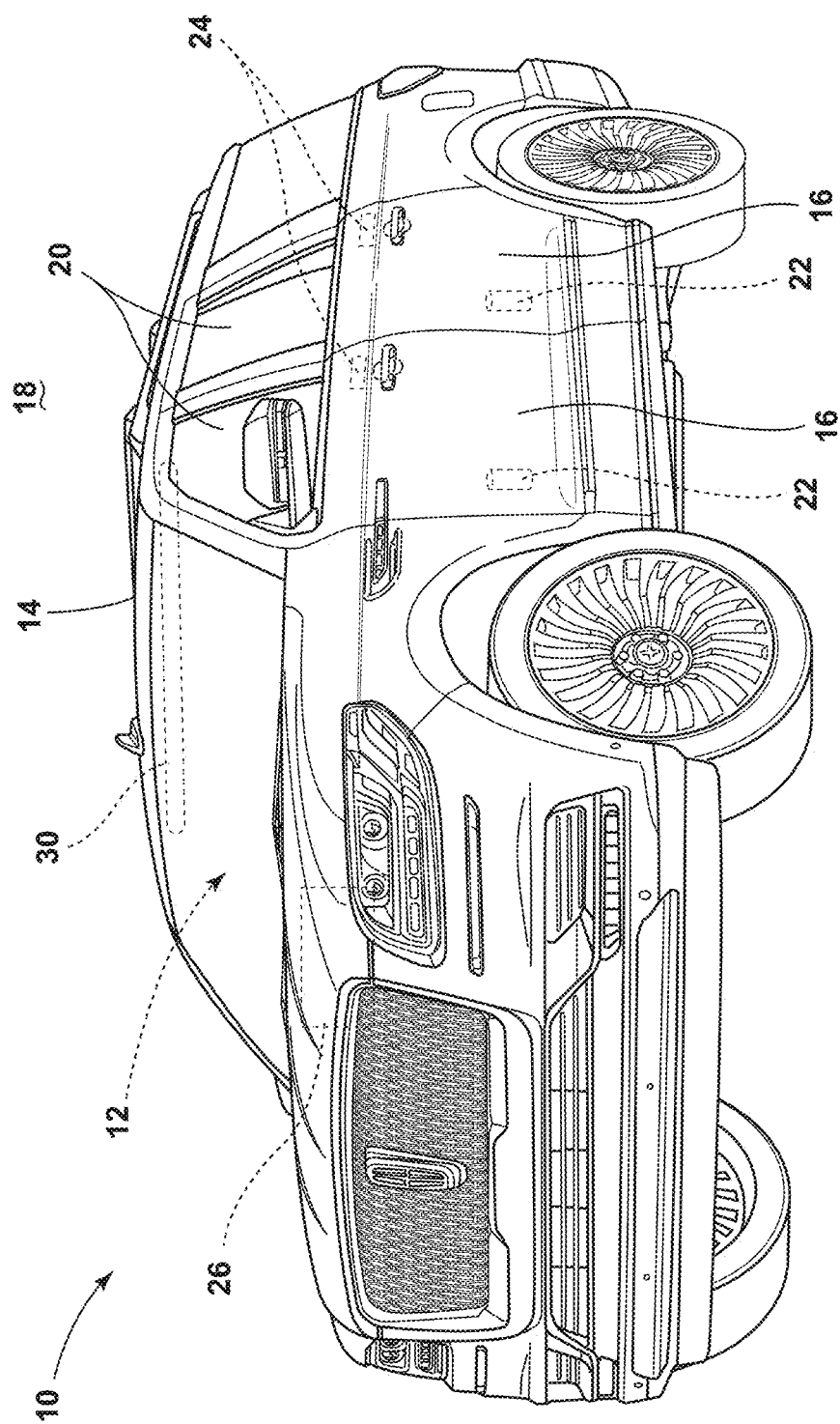
FIG. 1 is a perspective view of a vehicle, illustrating an air sanitizing apparatus disposed in an interior below a ceiling, and locks for doors and motors to raise or lower windowpanes.
Figure 2:
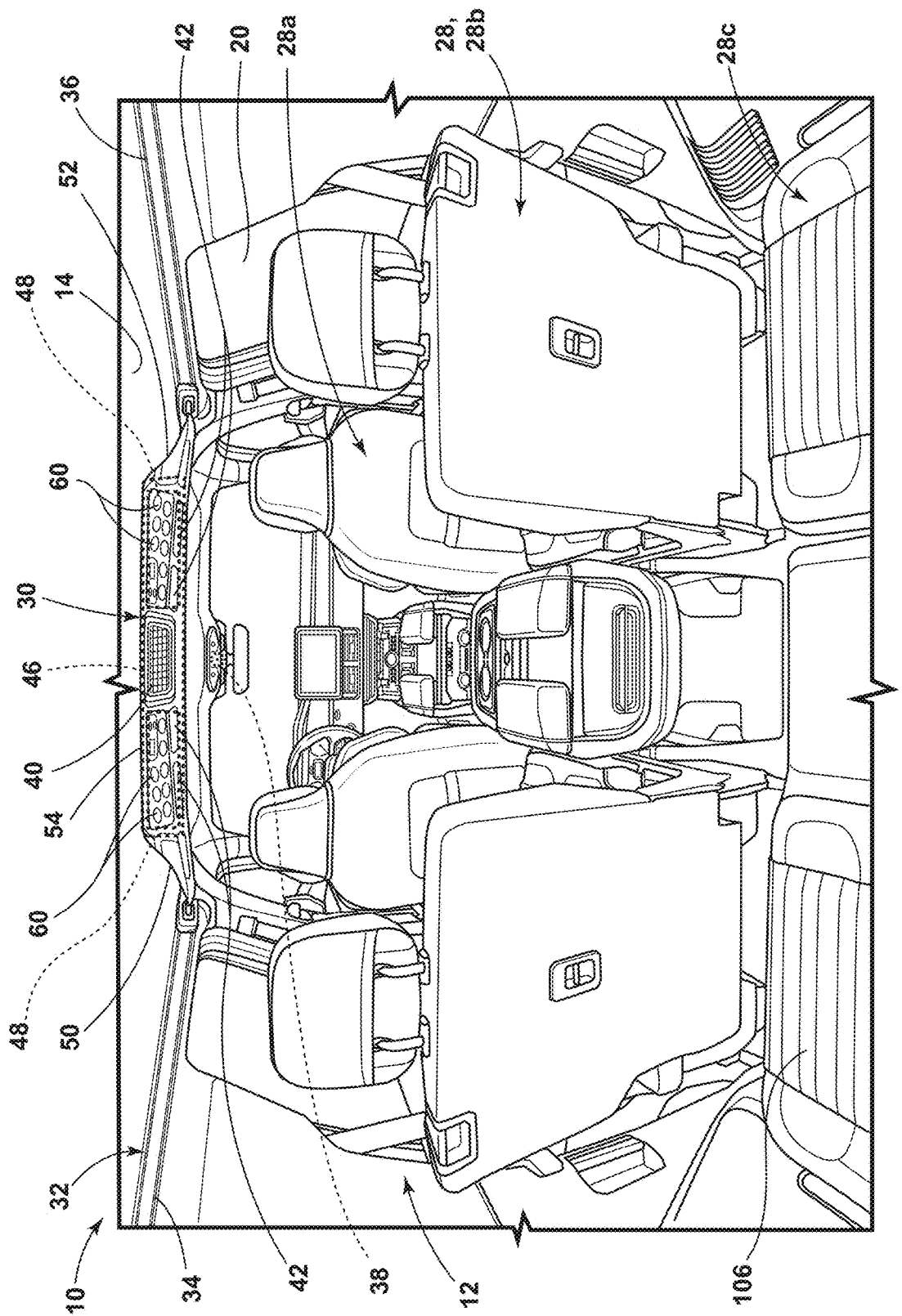
FIG. 2 is a perspective rear view of the interior of the vehicle of FIG. 1, illustrating a track system cooperating with the air sanitizing apparatus to allow the air sanitizing apparatus to move forward or rearward, and several rows of seating.

Referring to FIGS. 1 and 2, a vehicle 10 includes an interior 12. A ceiling 14 and doors 16 partially bound the interior 12, and separate the interior 12 from an exterior 18. Each door 16 includes a windowpane 20. A motor 22 is disposed in the door 16 to selectively raise or lower the windowpane 20. Each door 16 includes a lock 24, to selectively lock or unlock the door 16 to disallow or allow access to and from the interior 12. The vehicle 10 further includes a controller 26 to control various components of the vehicle 10, including the motors 22 for the windowpanes 20 and the locks 24 for the doors 16, as well as other components discussed further below. Although the illustrated vehicle 10 is a consumer automobile (e.g., Lincoln Navigator, Ford Motor Company, Dearborn, Michigan, USA), the vehicle 10 can be a bus, such as a bus used to provide intercity bus service (e.g., Prevost Car X3-45 by Volvo Buses, Gothenburg, Sweden, and operated by Greyhound Lines Inc., Dallas, Texas USA), a railway passenger car used in passenger transport (e.g., Viewliner II, CAF Beasain, Spain, operated by National Railroad Passenger Corporation d/b/a Amtrak, Washington D.C., USA), or an airplane used in passenger transport (e.g., Boeing 757, Boeing Commercial Airplanes, Renton, Washington, USA, operated by Delta Air Lines, Atlanta, Georgia, USA).

In the interior 12, the vehicle 10 includes at least one row of seating 28, and three rows of seating 28a-28c are illustrated in this embodiment. The vehicle 10 further includes an air sanitizing apparatus 30. The air sanitizing apparatus 30 is disposed below the ceiling 14 but adjacent to it. By being disposed adjacent to the ceiling 14, the air sanitizing apparatus 30 maximizes available headroom within the interior 12. The vehicle 10 further includes a track system 32 disposed near or at the ceiling 14. The track system 32 includes a first track 34 and a second track 36. As discussed further below, the air sanitizing apparatus 30 cooperates with the track system 32 to move and position the air sanitizing apparatus 30 selectively forward or rearward within the interior 12. The vehicle 10 can further include an occupancy sensor 38, to determine whether there are any occupants occupying the interior 12 of the vehicle 10, for reasons discussed further below.

Figure 3:
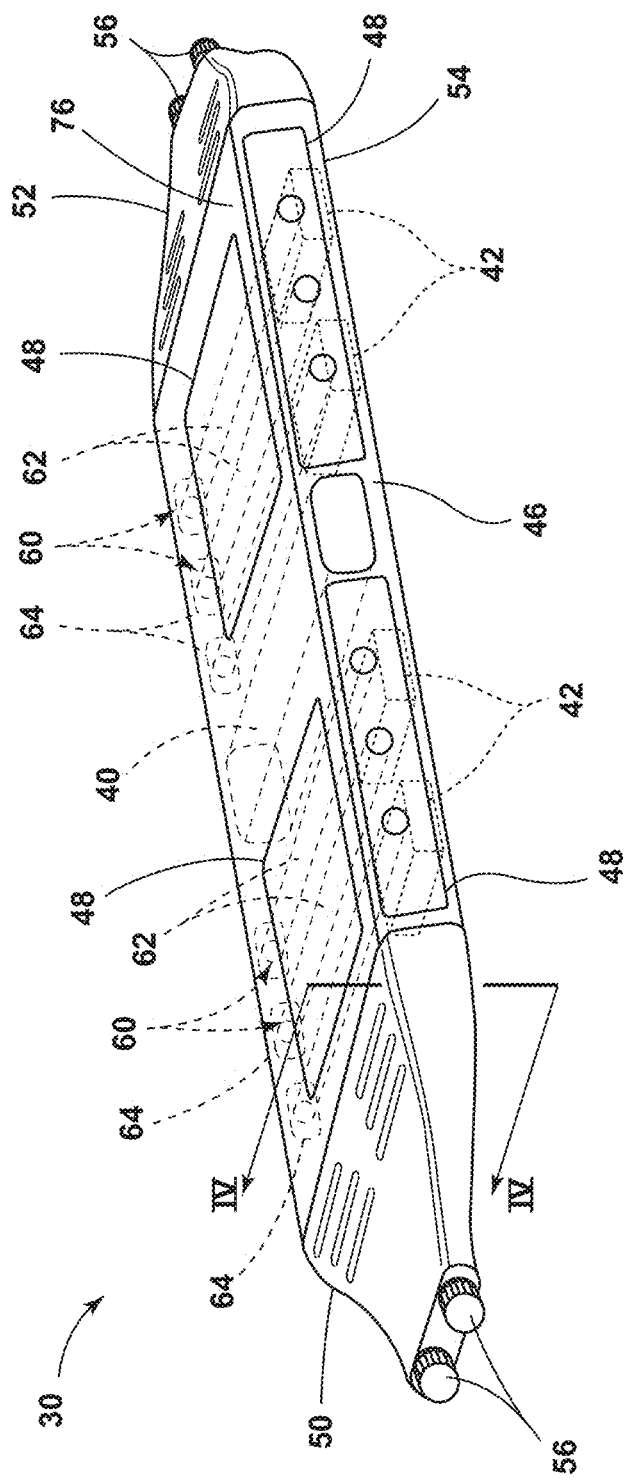
FIG. 3 is a perspective view of the air sanitizing apparatus of FIG. 1, illustrating an ozone generator, negative ion generators, and ultraviolet treatment modules disposed at a middle portion and within a housing with removable service panels to allow access into the housing, as well as a first end portion and a second end portion, from which rotating features extend to cooperate with the track system.
Figure 4:
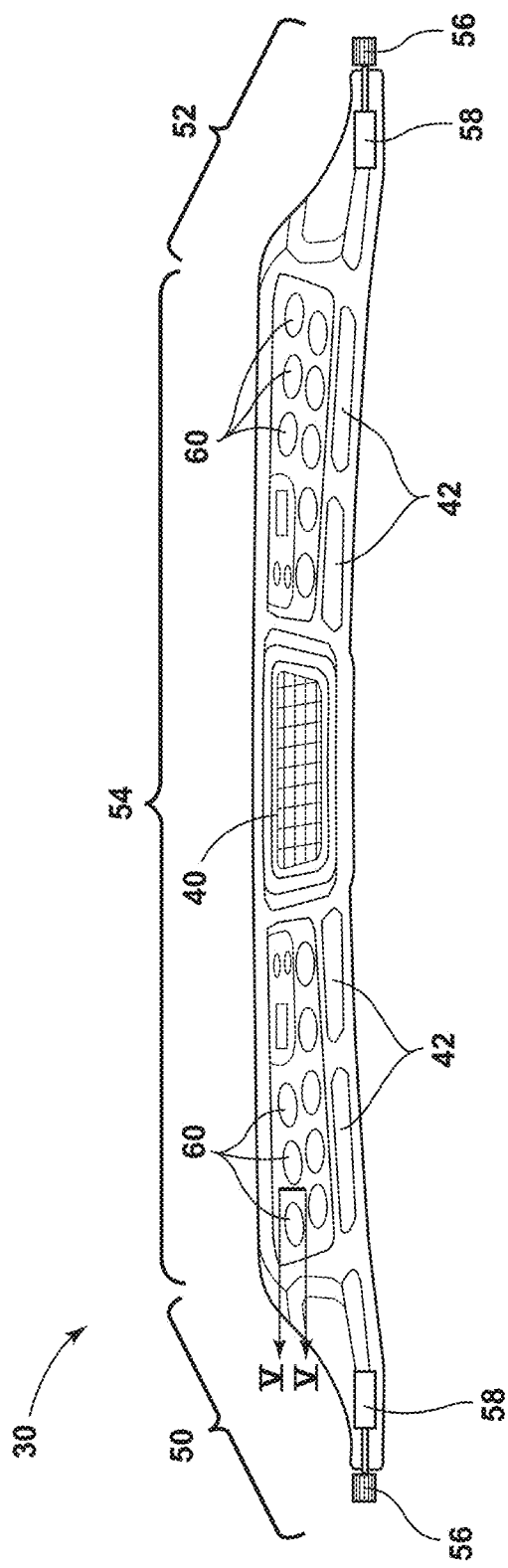
FIG. 4 is a rear view of a cross section of the air sanitizing apparatus of FIG. 1 taken along line IV-IV of FIG. 3, illustrating motors driving the rotating features to move and position the air sanitizing apparatus along the track system.
Figure 5:
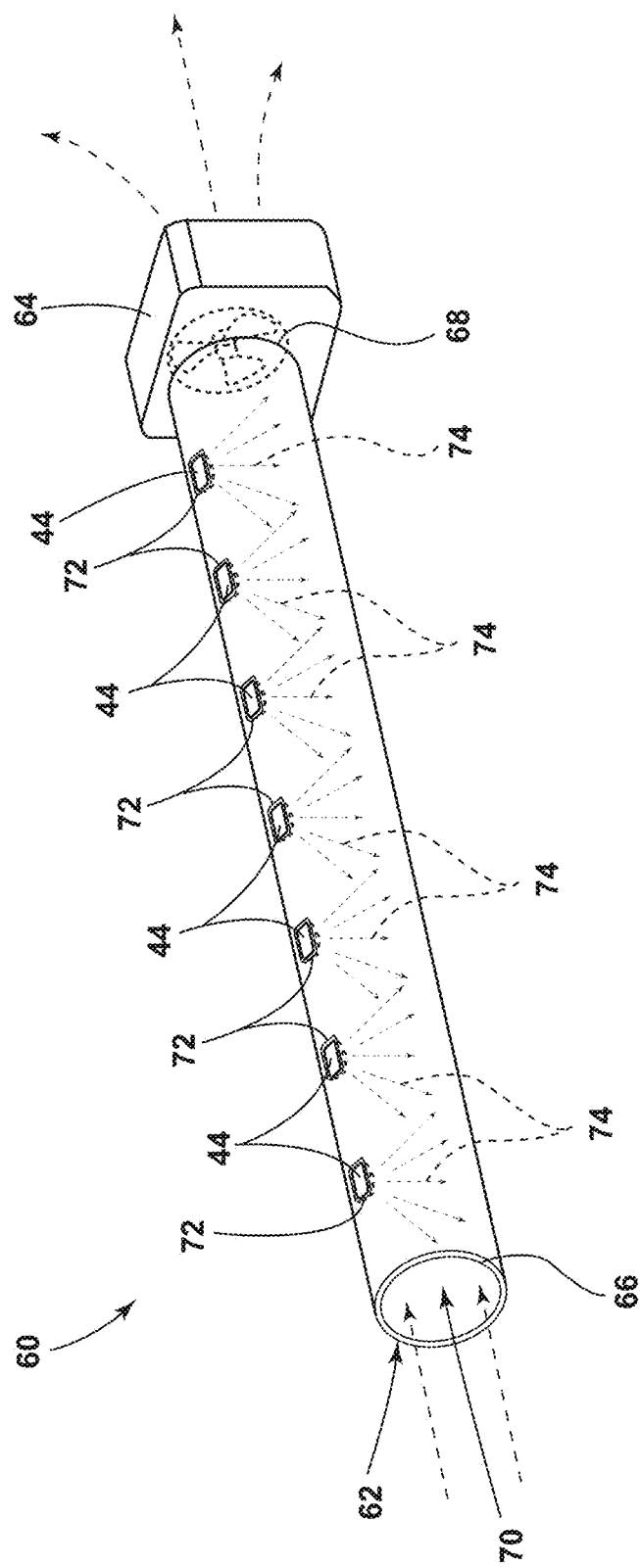
FIG. 5 is a perspective view of one of the ultraviolet treatment modules of FIG. 3, identified by cross-sectional line V-V of FIG. 4, illustrating ultraviolet radiation sources extending through apertures in an air flow tube so that ultraviolet radiation can be irradiated onto air pulled through the air flow tube by an exhaust fan.

Referring now to FIGS. 3-5, the air sanitizing apparatus 30 includes one or more of an ozone generator 40, at least one negative ion generator 42, and an ultraviolet radiation source 44, which are housed in a housing 46. The air sanitizing apparatus 30 further includes a variety of vented access panels 48 that can be removed to allow for changing of air filters, duct cleaning, and replacement of various components of the air sanitizing apparatus 30. As in the illustrated embodiment, the air sanitizing apparatus 30 can include all of the ozone generator 40, the at least one negative ion generator 42, and the ultraviolet radiation source 44. When activated, the ozone generator 40 generates ozone into the interior 12 from the oxygen present in the air of the interior 12 of the vehicle 10. The generated ozone can deodorize the vehicle 10. Without being bound by any particular theory, it is thought that ozone is highly reactive and reacts with chemicals and microorganisms that cause odor in the vehicle 10 to create a different chemical substance and thus eliminating the cause of the odor. When activated, the negative ion generator(s) 42 negatively ionize molecules such as oxygen and nitrogen in the air of the interior 12 of the vehicle 10. Without being bound by any particular theory, it is thought that negatively ionized molecules in the air attract particulates in the air and, then, the statically combined negatively ionized molecule and particulate float to and statically stick to a surface thus removing the particulates from the air.

The air sanitizing apparatus 30 further includes a first end portion 50, a second end portion 52, and a middle portion 54 disposed between the first end portion 50 and the second end portion 52. When cooperating with the track system 32, the first end portion 50 is disposed adjacent to the first track 34, and the second end portion 52 is disposed adjacent to the second track 36. The ozone generator 40, the negative ion generator 42, and the ultraviolet radiation source 44 are all disposed at the middle portion 54. The air sanitizing apparatus 30 further includes at least one rotating feature 56 and a motor 58 operably connected to the rotating feature 56 to drive the rotating feature 56. In the illustrated embodiment, both of the first end portion 50 and the second end portion 52 include a pair of rotating features 56 extending outward therefrom, and the motor 58 to separately operably connected to each rotating feature 56. Each of the rotating features 56 cooperate with the track system 32. More specifically, the rotating features 56 extending outward from the first end portion 50 extend into or onto the first track 34 of the track system 32, while the rotating features 56 extending outward from the second end portion 52 extend into or onto the second track 36 of the track system 32. In that manner, the rotating features 56 are configured to move the air sanitizing apparatus 30 along the track system 32.

Referring now additionally to FIG. 5, the ultraviolet radiation source 44, in the illustrated embodiment, is a component of an ultraviolet radiation treatment module 60 of the air sanitizing apparatus 30. The ultraviolet radiation treatment module 60 is disposed at the middle portion 54 of the air sanitizing apparatus 30. The ultraviolet radiation treatment module 60 includes an air flow tube 62, numerous ultraviolet radiation sources 44, and an exhaust fan 64. The air flow tube 62 has a first end 66, a second end 68, and an inside 70 through which air can flow that extends from the first end 66 to the second end 68. The exhaust fan 64 is disposed at either the first end 66 or the second end 68 (in the illustrated embodiment, at the second end 68) of the air flow tube 62. When activated, the exhaust fan 64 causes air to flow through the inside 70 of the air flow tube 62. The ultraviolet radiation treatment module 60 includes many ultraviolet radiation sources 44 disposed along the air flow tube 62. The air flow tube 62 includes apertures 72, through each of which one of the ultraviolet radiation sources 44 projects. The ultraviolet radiation source(s) 44 then, when activated, irradiate ultraviolet radiation 74 into the inside 70 of the air flow tube 62. Thus, when the exhaust fan 64 is activated and causing air flow, the ultraviolet radiation source(s) 44 irradiate the air flowing inside the air flow tube 62 with ultraviolet radiation 74 (specifically, electromagnetic radiation having a wavelength between 100 nm and 280 nm, commonly referred to as UV-C radiation). The ultraviolet radiation 74 harms microorganisms floating through the air. Without being bound by any particular theory, it is believed that the ultraviolet radiation 74 damages the deoxyribonucleic acid (DNA) of the microorganism and, thereby, eliminates the ability of the microorganism to replicate.

Figure 6:
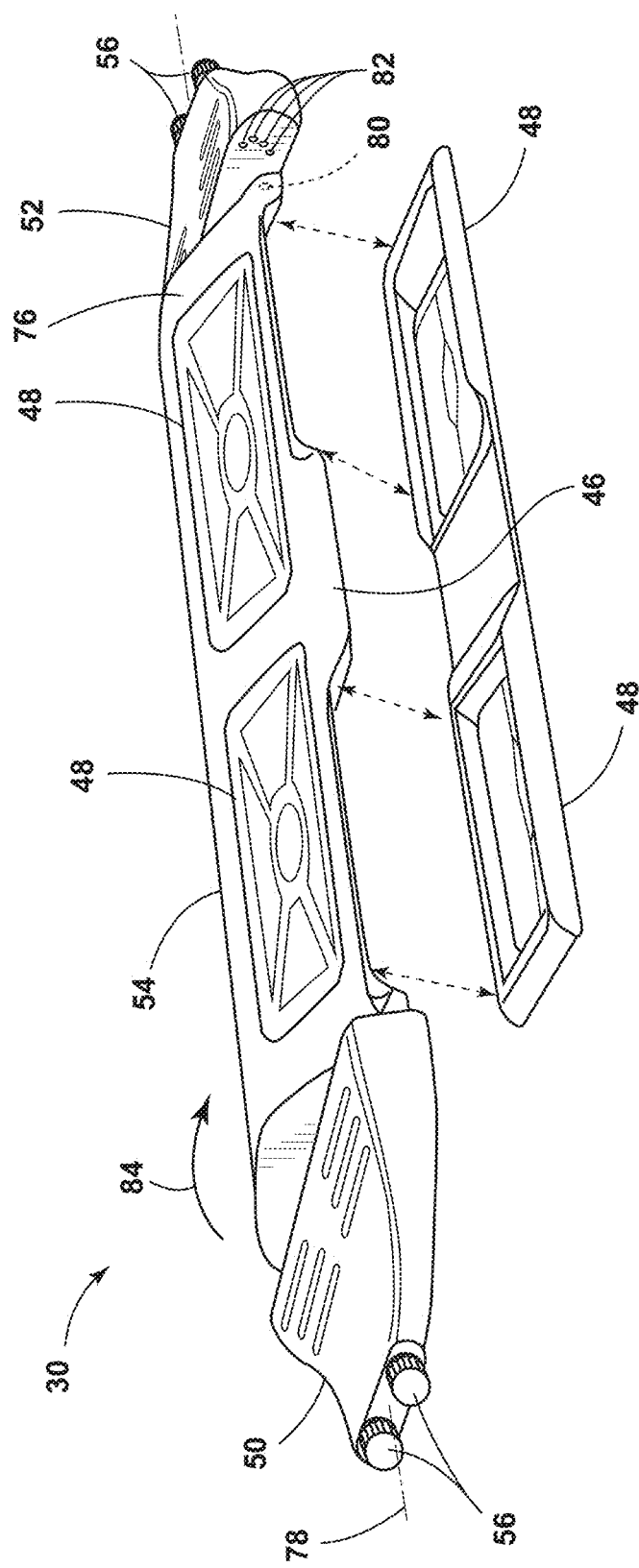
FIG. 6 is a perspective view of the air sanitizing apparatus of FIG. 1, illustrating the middle portion in a rotated position about an axis relative to the first end portion and the second end portion, the rotated position allowing easier access to the removable service panels at the housing.

Referring additionally now to FIG. 6, the middle portion 54 is rotatable relative to the first end portion 50 and the second end portion 52. In other words, the middle portion 54 can rotate while the first end portion 50 and the second end portion 52 remain operably connected to the track system 32. Because the middle portion 54 is rotatable, the vented access panels 48, such as those disposed at a top portion 76 of the middle portion 54 can be temporarily removed more easily. Otherwise, the vented access panels 48 at the top portion 76 could become inaccessible due to the close proximity of the ceiling 14 on the interior 12. The middle portion 54 is rotatable about an axis 78. The axis 78 extends through both the first end portion 50 and the second end portion 52. The axis 78 is approximately orthogonal to the first track 34 and the second track 36 of the track system 32. The middle portion 54 includes at least one rounded extension 80 that cooperates with a rounded indent 82 disposed at either the first end portion 50 or the second end portion 52 to allow the middle portion 54 to be maintained in a rotated position 84 during servicing. In the illustrated embodiment, the second end portion 52 includes several rounded indents 82 that are positioned to receive the rounded extension 80 of the middle portion 54 extending towards the second end portion 52. In addition, the first end portion 50 includes several rounded indents 82 (not illustrated) that are positioned to receive the rounded extension 80 of the middle portion 54 extending towards the first end portion 50. Each of the first end portion 50 and the second end portion 52 include several rounded indents 82 to receive the respective rounded extension 80 depending on a degree of the rotation position 84 of the middle portion 54. In other words, at one degree of the rotation position 84, the rounded extension 80 extends into one of the rounded indents 82, but at another degree of the rotation position 84, the rounded extension 80 extends into another one of the rounded indents 82. A person, such as a person servicing the air sanitizing apparatus 30, can rotate the middle portion 54 manually by rotating the middle portion 54. The middle portion 54 can include a locking mechanism (not illustrated) that prevents rotation of the middle portion 54 unless the person unlocks the locking mechanism. Alternatively or additionally, the controller 26 can cause the middle portion 54 to rotate upon command, such as via manipulation of a motor (not illustrated) in the middle portion 54, the first end portion 50, or the second end portion 52 that rotates the middle portion 54.

Figure 7:
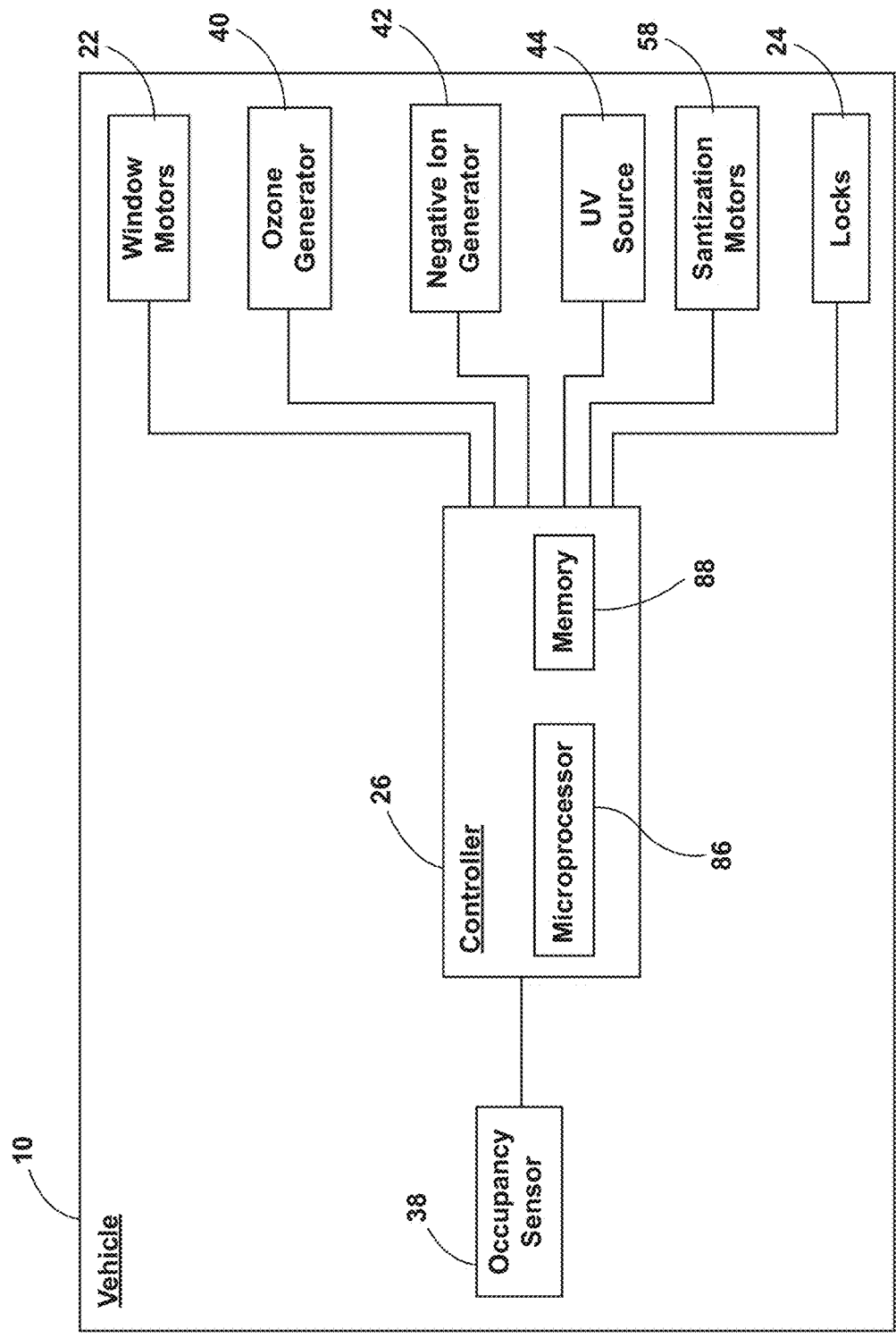
FIG. 7 is a schematic diagram of a controller of the vehicle of FIG. 1, illustrating the controller controlling the motors for the windowpanes, the ozone generator, the negative ion generator, the ultraviolet radiation source(s), the motor(s) that drive the air sanitizing apparatus, the locks of the doors, and receiving data from the occupancy sensor.

Referring now to FIG. 7, as mentioned above, the vehicle 10 includes the controller 26. The controller 26 includes a microprocessor 86 in communication with a memory 88. The microprocessor 86 executes programs stored in the memory 88. The controller 26 is in communication with and controls the ozone generator 40, the negative ion generator 42, the ultraviolet radiation source(s) 44, the exhaust fan 64 cooperating with the ultraviolet radiation source(s) 44, and the motor(s) 58 connected to and driving the rotating feature(s) 56. In addition, the controller 26 is in communication with and controls the locks 24 of the doors 16, and the motors 22 that raise or lower the windowpanes 20. The controller 26 is in communication with and receives data from the occupancy sensor 38 as to whether an occupant is occupying the interior 12.

Figure 8:
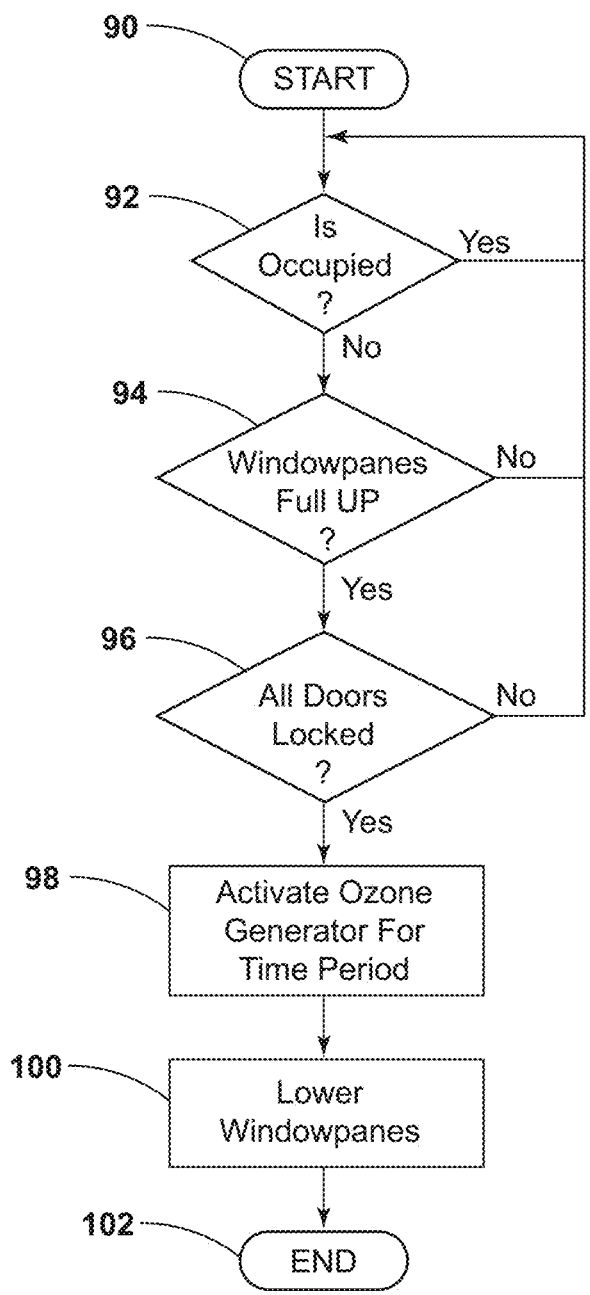
FIG. 8 is a diagram for an algorithm that the controller of FIG. 7 executes in order to determine whether to activate the ozone generator.

Referring now additionally to FIG. 8, the controller 26 is configured to activate the ozone generator 40 to generate ozone, only if specific conditions are met, such as the vehicle 10 is unoccupied and the interior 12 cannot be accessed. For example, pursuant to the illustrated algorithm, which may be stored in the memory 88 as a program that the microprocessor 86 executes, at step 90, the controller 26 starts the ozone generation sequence. At step 92, the controller 26 receives data from the occupancy sensor 38 and queries whether the data indicates whether an occupant is occupying the interior 12. If the data reveals that an occupant is occupying the interior 12, then the program returns to the start at step 90. If the data reveals that no occupancy is occupying the interior 12, then the program proceeds to step 94. At step 94, the controller 26 determines whether the motors 22 have fully raised the windowpanes 20. If not, then the program returns to start at step 90. The controller 26 may optionally then cause the motors 22 to fully raise the windowpanes 20. If yes, the motors 22 have fully raised the windowpanes 20, then the program proceeds to step 96. At step 96, the controller 26 queries whether the locks 24 are in a locked position to prevent the doors 16 from opening and allowing access into the interior 12. If not, then the program returns to start at step 90. The controller 26 may optionally then cause the locks 24 to move to a locked positon and prevent the doors 16 from opening. If yes, the locks 24 are locking the doors 16, then the program proceeds to step 98. At step 98, the controller 26 activates the ozone generator 40. The controller 26 can cause the ozone generator 40 to generate ozone for a certain period time or until certain other conditions are satisfied. The controller 26 can then, after a certain period of time after cessation of ozone generation, optionally (at step 100) cause the motors 22 to lower the windowpanes 20. The controller 26 can perform this ozone generation operation automatically when certain time and location criteria are met, such as at a home base during a period of time when the vehicle 10 historically is not being operated (e.g., in the garage of the owner at 2 AM). At step 102, the algorithm ends.

Figure 9:
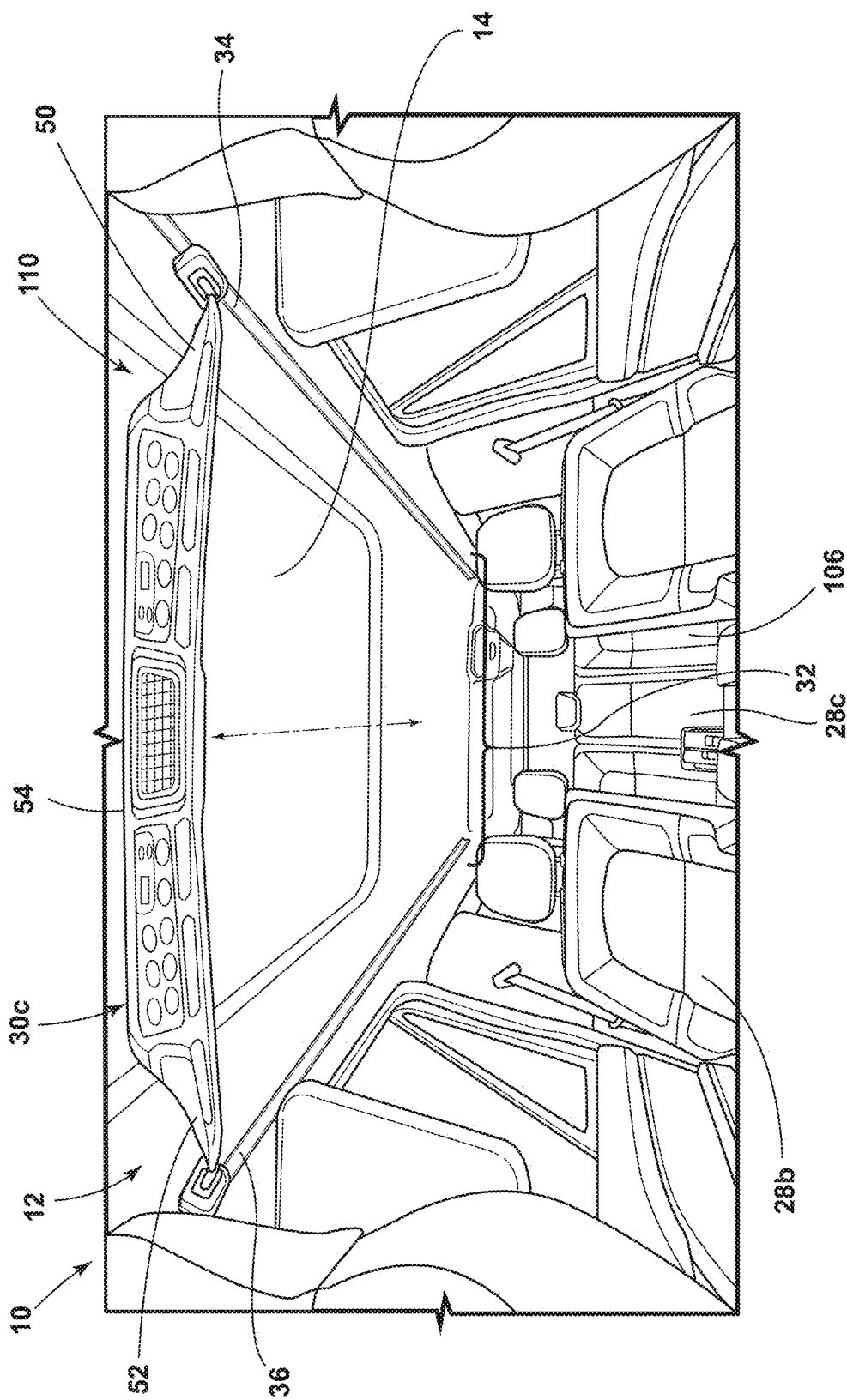
FIG. 9 is a forward perspective view of the interior of the vehicle of FIG. 1, illustrating the air sanitizing apparatus in a first position forward a first row of seating.
Figure 10:
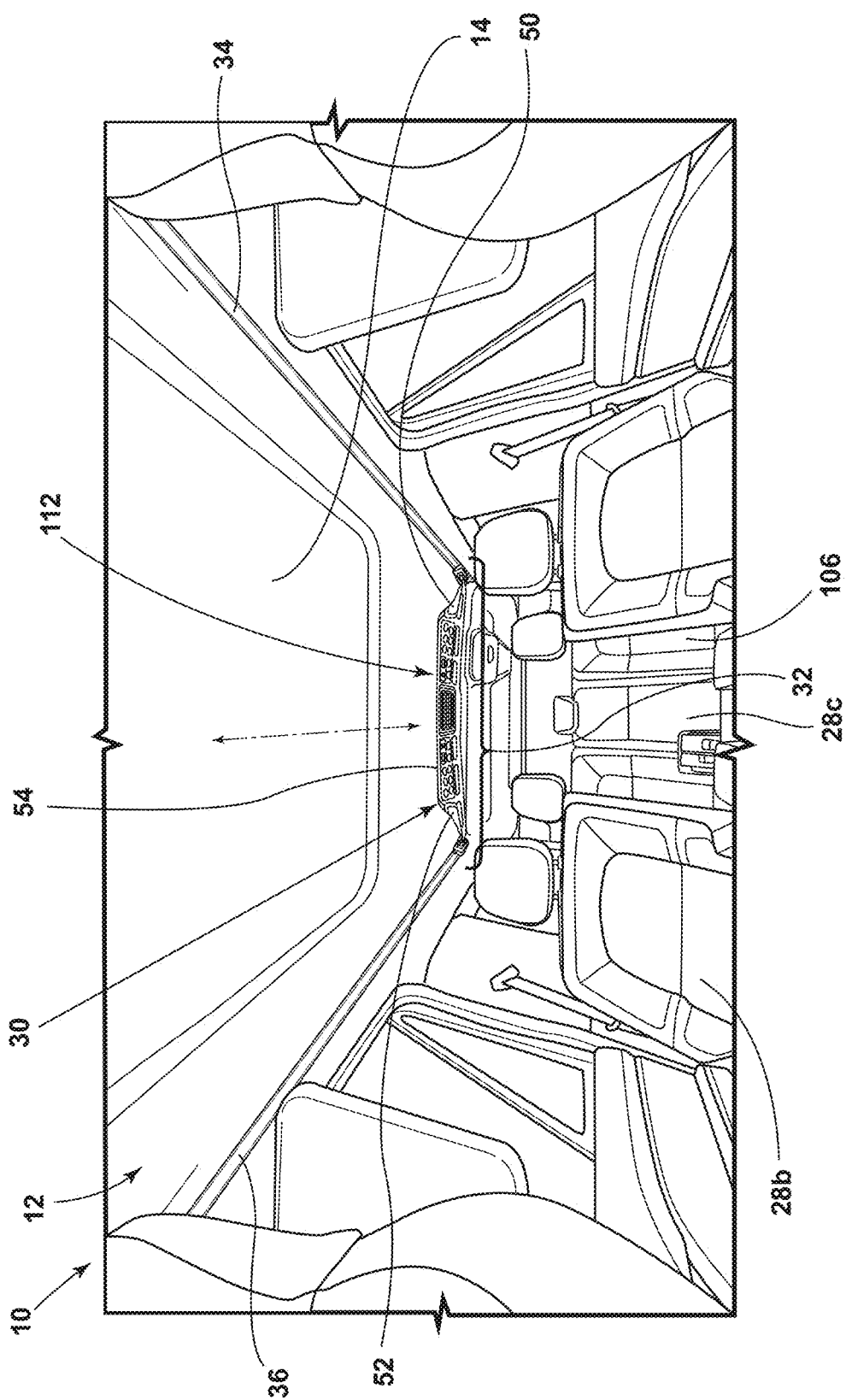
FIG. 10 is a continuation of a sequence started in FIG. 9, illustrating the air sanitizing apparatus having been moved along the track system to a second position rearward of the first row of seating and positioned above a second row of seating, in order to sanitize the air above the second row of seating including a seat of the second row of seating.

Referring now to FIGS. 9 and 10, the controller 26, being in control of the motors 58 of the air sanitizing apparatus 30, can cause the air sanitizing apparatus 30 to move along the track system 32. In the example positing illustrated in FIG. 9, the air sanitizing apparatus 30 is disposed forward of the row of seating 28*b*. However, in FIG. 10, the controller 26 has manipulated the motors 58 to cause the air sanitizing apparatus 30 to move along the track system 32 past the row of seating 28*b* and above the row of seating 28*c* disposed rearward in the interior 12 of the vehicle 10. While the air sanitizing apparatus 30 is above the row of seating 28*c*, the controller 26 can cause the negative ion generator 42 to negatively ionize molecules of the air of the interior 12 of the vehicle 10. In addition, while the air sanitizing apparatus 30 is above the row of seating 28*c*, the controller 26 can cause the negative ion generator 42 to irradiate the air of the interior 12 with the ultraviolet radiation 74. The controller 26 can manipulate the motors 58 to position the air sanitizing apparatus 30 to any position along the track system 32 and cause any or all of the ozone generator 40, the negative ion generator 42, and the ultraviolet radiation source 44 to perform their air sanitizing functions described above.

Figure 11:
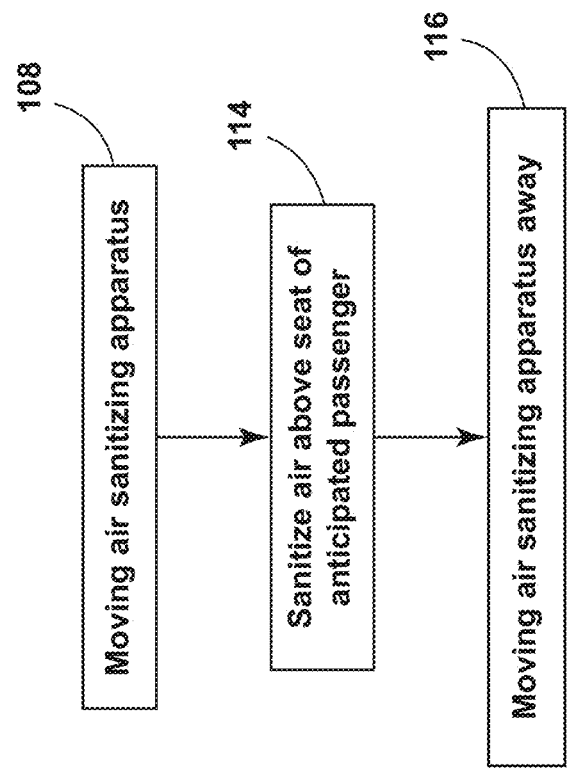
FIG. 11 is a diagram for an algorithm that the controller of FIG. 7 executes in order as part of a method of sanitizing the air in the vehicle.
Figure 12:
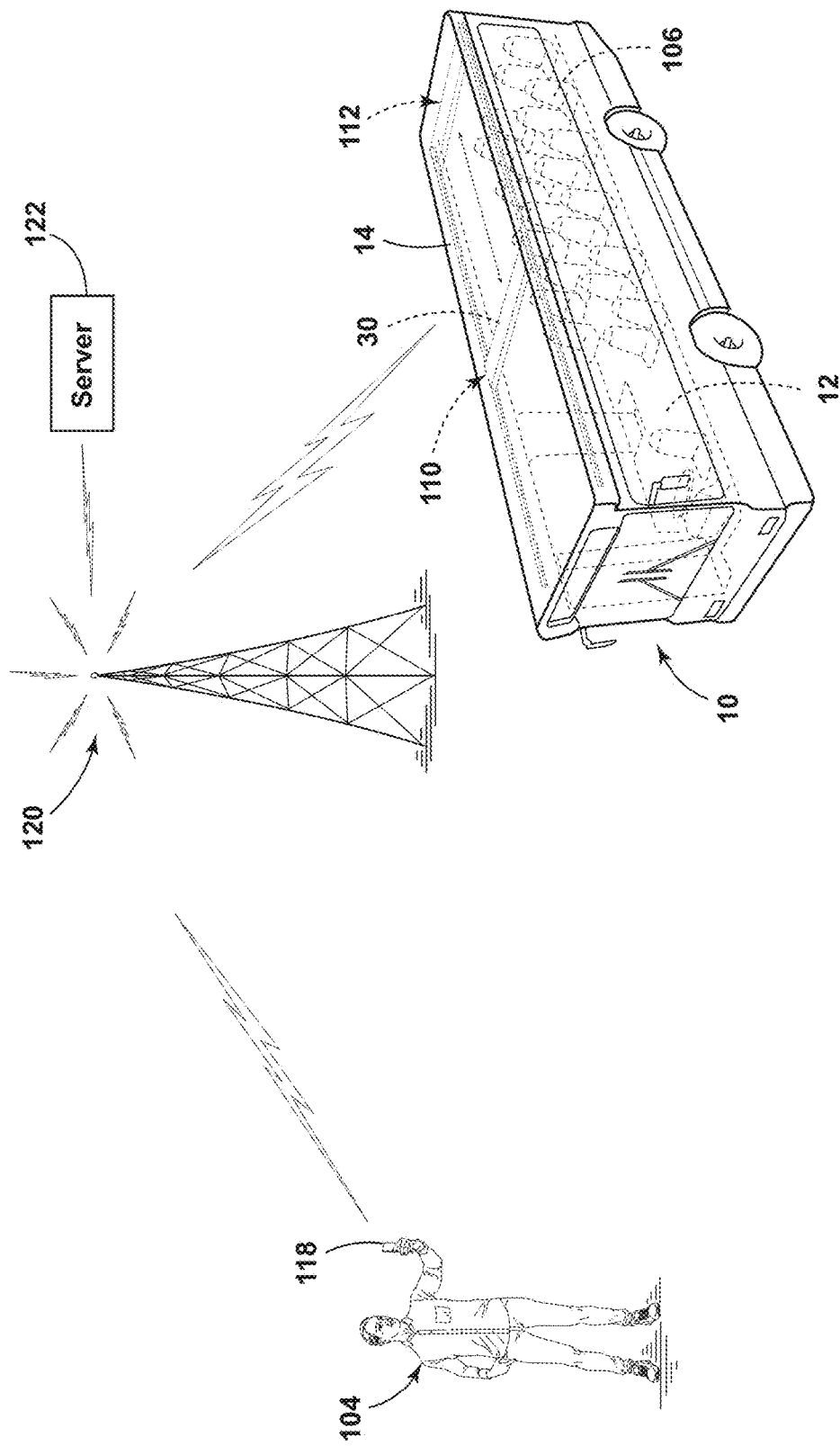
FIG. 12 is a schematic diagram, illustrating an anticipated passenger of the vehicle (a bus), before the anticipated passenger enters the vehicle, using an electronic device (e.g., smartphone) to request the air sanitizing apparatus to sanitize the air above the seat, which the anticipated passenger has reserved also with the electronic device.

Referring now to FIGS. 11 and 12, the air sanitizing apparatus 30 can be utilized in a novel method of sanitizing air in the vehicle 10. Upon request of an anticipated passenger 104 of a seat 106 of the vehicle 10, and before the anticipated passenger 104 occupies the seat 106, the method (at step 108 includes moving the air sanitizing apparatus 30 from a first position 110 that is not above the seat 106 of the vehicle 10 to a second position 112 above the seat 106 of the vehicle 10. As explained above, the air sanitizing apparatus 30, including the rotating feature(s) 56 thereof, cooperate with the track system 32 to move from the first position 110 to the second position 112 over the seat 106. At step 114, the method includes causing the air sanitizing apparatus 30 to perform at least one of the air sanitizing actions described above, such as causing the air sanitizing apparatus 30 to perform at least one of the following actions: generate ozone; negatively ionize molecules in the interior 12 air; and irradiate the interior 12 air with ultraviolet radiation 74. At step 116, the method includes moving the air sanitizing apparatus 30 away from the second position 112, such as back to the first position 110, before the anticipated passenger 104 occupies the seat 106. The controller 26 can cause the motor(s) 58 to move the air sanitizing apparatus 30 back to a home position (e.g., the first position 110) after sanitizing the air above the seat 106 of the anticipated passenger 104.

The anticipated passenger 104 can request the air sanitizing apparatus 30 to move over the seat 106 and perform the at least one action of air sanitization via an application program stored on and/or executed by an electronic device 118 (e.g., a smartphone). The electronic device 118 is located outside of the interior 12 of the vehicle 10. As an example, the anticipated passenger 104 can use an application program provided by an operator of the vehicle 10 or service provider that utilizes the vehicle 10 for the service to reserve the seat 106 on the vehicle 10. As part of the reservation process, the application program can query whether the anticipated passenger 104 desires to sanitize the air above the seat 106 reserved, perhaps for an extra fee. If the anticipated passenger 104 selects yes, the yes response can be sent via a cellular network 120 from the electronic device 118 to a server 122, and then from the server 122 to the controller 26 of the vehicle 10 via the cellular network 120. The controller 26 can then cause the air sanitizing apparatus 30 to move to the second position 112 over the seat 106 and sanitize the air above the seat 106, such as by negatively ionizing molecules in the interior 12 air; and irradiating the interior 12 air with the ultraviolet radiation 74. When the vehicle 10 is out-of-service, the controller 26 can cause the air sanitizing apparatus 30 to generate ozone, as discussed above.

Figure 13:
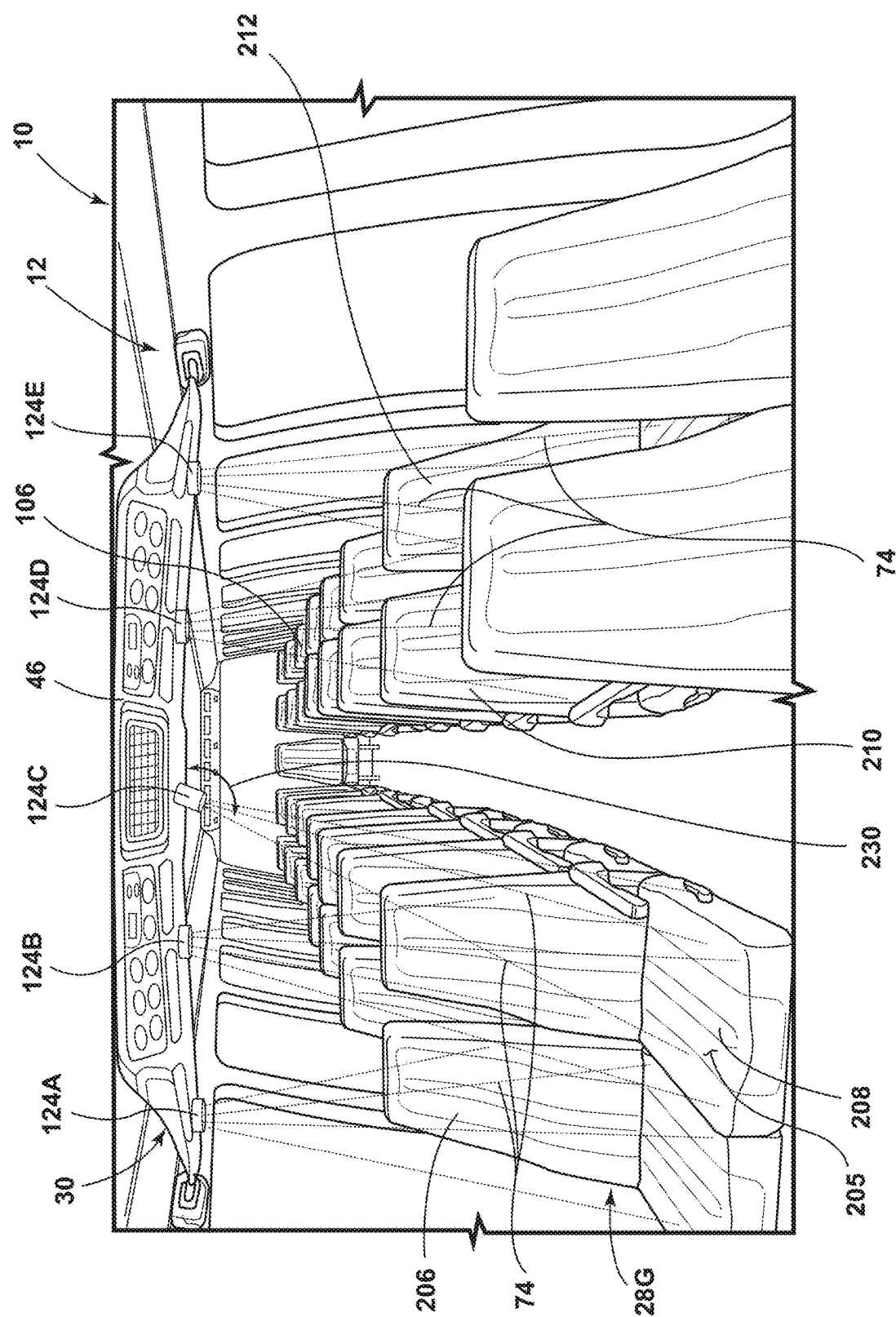
FIG. 13 is a perspective view of an interior of the vehicle (bus of FIG. 12), illustrating an embodiment of the air sanitizing apparatus of FIG. 1 additionally including ultraviolet radiation sources, each of which are configured to emit ultraviolet radiation at a particular seat in a particular row of seating, and a positionable ultraviolet radiation source that can be positioned upon command to emit ultraviolet radiation at any particular seat of the particular row of seating.

Referring now to FIG. 13, an embodiment of the air sanitizing apparatus 30 can further include ultraviolet radiation sources 124A-E. Each of the ultraviolet radiation sources 124A-E are in communication with the controller 26 and can emit ultraviolet radiation 74. Each of ultraviolet radiation sources 124A, B, D, and E are configured to emit ultraviolet radiation 74 so the ultraviolet radiation 74 irradiates a particular seat in any given row of seating 28. For example, when the air sanitizing apparatus 30 is moved above row of seating 28G, ultraviolet radiation source 124A emits ultraviolet radiation 74 onto a surface 205 of a seat 206 of row of seating 28G. Ultraviolet radiation source 124B emits ultraviolet radiation 74 onto the surface 205 of a seat 208 of row of seating 28G, ultraviolet radiation source 124D emits ultraviolet radiation 74 onto the surface 205 of a seat 210 of row of seating 28G, and ultraviolet radiation source 124D emits ultraviolet radiation 74 onto the surface 205 of a seat 212 of row of seating 28G. Thus, the air sanitizing apparatus 30 can disinfect the surfaces 205 of all the seats of any given row of seating 28 at the same time. Once the air sanitizing apparatus 30 has so disinfected the surface 205 of the seats of one row of seating 28 (such as after a predetermined amount of time emitting ultraviolet radiation 74), the air sanitizing apparatus 30 can move to another row of seating 28 to sanitizing the seats of that row of seating 28, and so on. Ultraviolet radiation source 124C is positionable such that ultraviolet radiation source 124C can emit ultraviolet radiation 74 onto any one of the seats of any given row of seating 28 upon command from the controller 26. In the figure, the ultraviolet radiation source 124C is emitting ultraviolet radiation onto seat 208 of the row of seating 28G. However, the ultraviolet radiation source 124C can be commanded to reposition 230 so as to emit ultraviolet radiation onto any of the seats 206, 210, or 212 of the row of seating 28G. Therefore, in further reference to FIG. 12 and the related discussion above, the anticipated passenger 104 can request the air sanitizing apparatus 30 to move over seat 106 and sanitize the surface 205 of the seat 106, such as part of the reservation process. The controller 26 can then command the air sanitizing apparatus 30 to move over the row of seating of which seat 106 is a part, and cause ultraviolet radiation source 124C and/or 124E to emit ultraviolet radiation 74 onto the surface 205 of the seat 106.

With the air sanitizing apparatus 30 and methods described above, owners and operators of vehicle-for-hire, commercial airplane, or passenger railcar can maintain a higher degree of air sanitization then before. In addition, anticipated passengers will be comforted knowing that the air in such spaces has been sanitized, and the anticipated passengers have a measure of control over sanitization of the air in such spaces before they enter and become passengers.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is to be understood that variations and modifications can be made on the afore-mentioned structure without departure from the concepts of the present disclosure, and further it is to be understood that such concepts are intended to be covered by the following claims unless these claims by their language expressly state otherwise.

What is claimed is:

1. A method of sanitizing air in a vehicle comprising:
   upon request of an anticipated passenger of a seat in a vehicle, before the anticipated passenger occupies the seat, moving an air sanitizing apparatus from a first position that is not above the seat of the vehicle to a second position above the seat of the vehicle;
   causing the air sanitizing apparatus to perform at least one of the following actions: generate ozone, negatively ionize molecules in interior air, irradiate interior air with ultraviolet radiation, and irradiate a surface of the seat with ultraviolet radiation; and
   moving the air sanitizing apparatus away from the second position, before the anticipated passenger occupies the seat,
   wherein, the anticipated passenger requested the air sanitizing apparatus to perform the at least one action via an application program on an electronic device located outside of an interior of the vehicle.

2. The method of claim 1, wherein
the anticipated passenger reserved the seat via the electronic device.

3. The method of claim 1,
wherein, the vehicle includes a track system, and the air sanitizing apparatus cooperates with the track system to move from the first position to the second position over the seat.

4. The method of claim 1,
wherein, the vehicle is a bus, a railway passenger car, or an airplane; and
wherein, the air sanitizing apparatus is caused to perform both the actions of: negatively ionizing molecules in the interior air and irradiating interior air with ultraviolet radiation.

5. The method of claim 1, wherein
the air sanitizing apparatus is mounted within the vehicle.

6. The method of claim 1, wherein
the air sanitizing apparatus comprises an ultraviolet radiation source; and
the air sanitizing apparatus irradiates interior air with ultraviolet radiation from the ultraviolet radiation source.

7. The method of claim 1, wherein
the air sanitizing apparatus comprises an ultraviolet radiation source; and
the air sanitizing apparatus irradiates a surface of the seat with ultraviolet radiation from the ultraviolet radiation source.

8. The method of claim 1, wherein
the vehicle comprises a ceiling, and the air sanitizing apparatus is disposed below but adjacent to the ceiling.

9. The method of claim 1, wherein
the air sanitizing apparatus comprises a motor and a rotating feature operably connected to the motor, and the rotating feature cooperates with a track system to move the air sanitizing apparatus along the track system from the first position to the second position.

10. The method of claim 1, wherein
the air sanitizing apparatus is caused to generate ozone.

11. The method of claim 10 further comprising:
before causing the air sanitizing apparatus to generate ozone, (i) determining that locks of the vehicle prevent access into the interior of the vehicle and (ii) determining that no occupant is occupying the interior of the vehicle.

12. The method of claim 1, wherein
the vehicle further comprises a row of seating, of which the seat is part; and
the air sanitizing apparatus further comprises a positionable ultraviolet radiation source that can be positioned upon command to emit ultraviolet radiation to any particular seat of the row of seating.

13. A method of sanitizing air in a vehicle comprising:
upon request of an anticipated passenger of a seat in a vehicle, before the anticipated passenger occupies the seat, moving an air sanitizing apparatus from a first position that is not above the seat of the vehicle to a second position above the seat of the vehicle; and
causing the air sanitizing apparatus to perform at least one of the following actions: generate ozone, negatively ionize molecules in interior air, irradiate interior air with ultraviolet radiation, and irradiate a surface of the seat with ultraviolet radiation;
wherein, the vehicle further comprises a track system, the track system comprising a first track and a second track;
wherein, the air sanitizing apparatus further comprises (i) a first end portion that is disposed adjacent to the first track, (ii) a second end portion that is disposed adjacent to the second track, and (iii) a middle portion that is disposed between the first end portion and the second end portion; and
wherein, the middle portion of the air sanitizing apparatus is rotatable about an axis that extends through both the first end portion and the second end portion, such that the middle portion can rotate while the first end portion and the second end portion remain operably connected to the track system.

14. The method of claim 13, wherein
one or more of the first end portion and the second end portion of the air sanitizing apparatus comprises a motor that is operably connected to a rotating feature that cooperates with the track system to move the air sanitizing apparatus.

15. The method of claim 14, wherein
the air sanitizing apparatus further comprises (i) a housing disposed at the middle portion and (ii) a service panel disposed at a top portion of the middle portion to allow access into the housing.

16. The method of claim 15, wherein
the air sanitizing apparatus further comprises an ozone generator, a negative ion generator, and an ultraviolet treatment module disposed within the housing at the middle portion; and
the ultraviolet treatment module comprises an air flow tube, an ultraviolet radiation source, and an exhaust fan to cause air to flow through the air flow tube, and, when activated, the ultraviolet radiation source irradiates ultraviolet radiation into the air flow tube to irradiate the air flowing through the air flow tube with ultraviolet radiation.

* * * * *